United States Patent [19]

Hwang

[11] Patent Number: 4,850,055
[45] Date of Patent: Jul. 25, 1989

[54] EAR-WARMER

[76] Inventor: Gil S. Hwang, 6214 W. Grand, Chicago, Ill. 60639

[21] Appl. No.: 53,063

[22] Filed: May 21, 1987

[51] Int. Cl.$^4$ .......................................... A41D 13/00
[52] U.S. Cl. ...................................................... 2/209
[58] Field of Search ...................... 2/209, 174, 423; 381/187

[56] References Cited

U.S. PATENT DOCUMENTS

| 520,785 | 6/1894 | Jung | 2/209 |
|---|---|---|---|
| 2,428,897 | 10/1947 | Ungemah | 2/209 |
| 2,439,289 | 4/1948 | Fanslow | 2/209 |
| 2,700,162 | 1/1955 | Fuller | 2/209 |
| 3,354,471 | 11/1967 | Longo | 2/209 X |
| 4,670,911 | 6/1987 | Dunford | 2/423 X |

FOREIGN PATENT DOCUMENTS

| 0148274 | 11/1902 | Fed. Rep. of Germany | 2/209 |
|---|---|---|---|
| 0081124 | 9/1953 | Norway | 2/209 |

Primary Examiner—Peter Nerbun
Attorney, Agent, or Firm—Laff, Whitesel, Conte & Saret

[57] ABSTRACT

An ear muff has a spring biased butterfly clip with a bonnet fitting over each leaf or wing of the clip. The bonnet may be made of any suitable soft and cushioning material such as plush, fur, wool, or the like. The softness of this material pads the ear so that the butterfly clip does not cut off circulation or pinch the ear. Each leaf of the clip has a plurality of teeth which are padded by the bonnet and which insure contact between the leaves at a plurality of points.

6 Claims, 1 Drawing Sheet

EAR-WARMER

This invention relates to ear warmers and more particularly to independent ear muffs which may be separately attached to each ear.

There are many different types of ear warmers, ranging from scarves or the like which are wrapped around the head to separate cloth envelopes which fit over each of the individual ears. In general, those ear warmers which wrap around the head tend to disarrange or muss the hair and often are difficult to put on or to take off. For example, if a pair of ear muffs interconnected a head encircling spring are put on or taken off by a person wearing a hat, it is necessary to hold the hat in one hand and, with the other hand, to perform an operation requiring two hands.

Some of the ear muffs are small envelopes having a shape and contour to fit over the individual ear. These devices do not in themselves muss the hair, but they are difficult to put on and they still require a use of two hands. By the time that the ear muffs are in place or are removed, many of the same frustrations are encountered which result from a use of the muffs which are interconnected by the spring. When a hat is worn, it often is jarred and may fall off or must be removed before the ear muffs are in place.

Accordingly, an object of the invention is to provide new and improved ear warmers.

Another object is to provide ear warmers which do not muss the hair. Here an object is to provide ear muffs which can be put on or taken off with one hand, even while wearing a hat. In this connection, an object is to provide ear muffs which reliably remain in place.

In keeping with an aspect of the invention, these and other objects of the invention are accomplished by an ear muff having a spring biased butterfly clip which has a bonnet fitting over each leaf or wing of the clip. The bonnet may be made of any suitable material such as plush, fur, wool, or the like. The softness of this material pads the ear so that the butterfly clip does not cut off circulation or pinch the ear.

A preferred embodiment is shown in the attached drawing wherein.

Figure 1:
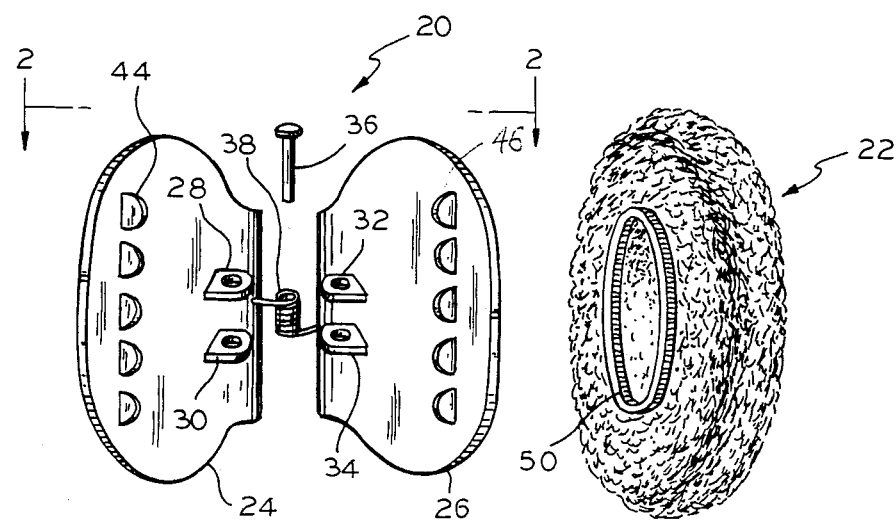
FIG. 1 is an exploded view of the inventive ear warmer.

In FIG. 1, the inventive ear warmer has a butterfly clip 20 and a bonnet 22. The butterfly clip 20 has two leaves or plates 24, 26 having upstanding members 28–34 which interleave to form a hinge. A hinge pin 36 passes through aligned holes in the upstanding members 28–34. A coiled spring 38 fits over the hinge pin 36 and normally biases the butterfly clip to a closed position.

Figure 2:
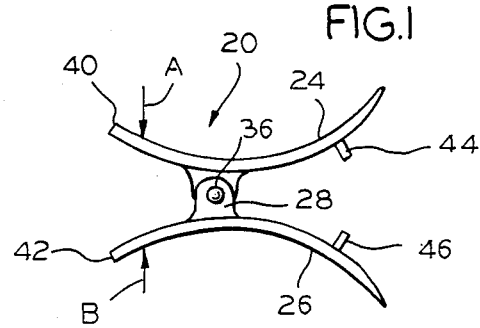
FIG. 2 is a top plan view of the butterfly clip, taken along line 2—2 of FIG. 1.

As best seen in FIG. 2, the leaves or plates 24, 26 may curve outwardly, away from the hinge pin 36. Tabs 40, 42 are formed on one end of the leaves 24, 26. When these tabs are squeezed together in directions A, B, the clip opens. When the tabs are released, the coiled spring 38 closes the clip.

Near the outer peripheral edge of each of the butterfly leaves 24, 26 is a row of outstanding teeth 44, 46 which are well rounded so that they will not bite into the ear. These teeth interdigitate when the leaves close. However, teeth 44, 46 do project outwardly to provide a plurality of fixed points for engaging the ear. Without these teeth, the leaves 24, 26 would tend to touch each other at a single point where they approach each other most closely. This would hold the remainder of the leaf surfaces in separation, thereby greatly reducing the holding power. With the interdigitating teeth, the ear is certain to be gripped in a plurality of places.

A pair of bonnets 22, 48 (FIG. 3) are formed with a central opening surrounded by an elastic band 50 around a center hole, for drawing it together, with enough gathering to enable the bonnet to be stretched over the leaves 24, 26. The bonnets not only cover the entirety of the leaves, but also the rows of teeth 44, 46. Since the bonnets are made of a thick, soft material (such as fur or plush), they cover and cushion the teeth so that they will not bite into the ear and cause pain. Thus, each bonnet forms a paid of soft pliable material for cushioning the ear against the bite of teeth 44, 46.

Figure 3:
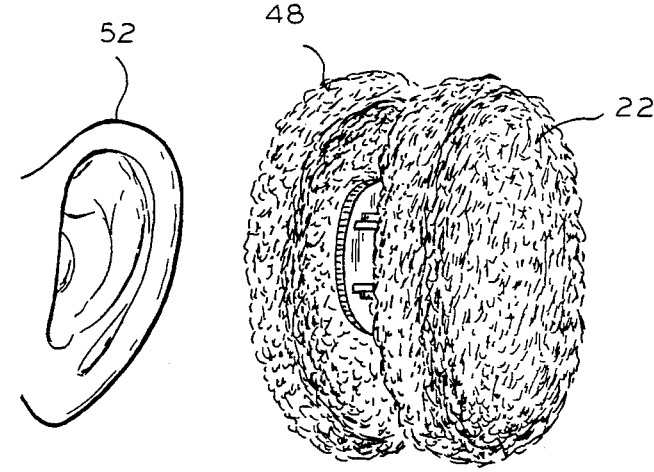
FIG. 3 shows the ear muff about to be placed onto a human ear.

As shown in FIG. 3, the inventive ear warmers are squeezed together, as indicated by the arrows A, B (FIG. 2) in order to separate the opposite edges of the leaves. The ear warmer is thus opened and slipped over the ear 52 and then released. The spring 38 closes the leaves and holds the ear warmer on the ear.

Figure 4:
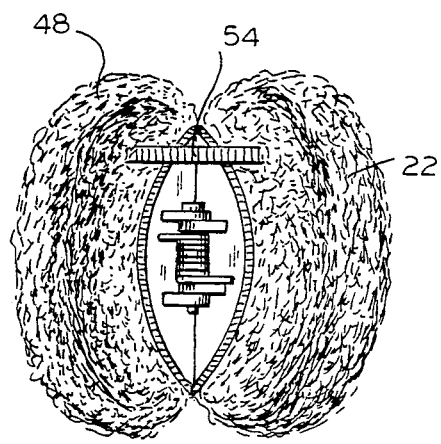
FIG. 4 is a front view of an opened butterfly clip with an attachment for helping to hold the ear warmer in place.

In FIG. 4, a flexible member in the form of rubber band 54 extends across the space between the leaves. When the ear warmer is opened, as shown in FIG. 4, the rubber band stretches somewhat. The ear warmer is placed onto the ear with band 54 extending over the top of the ear. When the ear warmer is released, the rubber band 54 hangs over the top of the ear, more or less like a string, in order to help hold the ear warmer in place.

Those who are skilled in the art will readily perceive how to modify the invention. Therefore, the appended claims are to be construed to cover all equivalent structures which fall within the true scope and spirit of the invention.

I claim:

1. An ear warmer comprising a hinged spring biased butterfly clip having a pair of opposed elongated leaves which are normally biased by said spring to a closed position, the elongation of said leaves extending in the same direction as a pivoting axis of said hinge, an aligned series of teeth formed adjacent the outer periphery of said leaves, the teeth on opposing leaves interdigitating when said leaves are closed, and a bonnet of soft and cushioning material covering each of said leaves, said bonnets covering said teeth to cushion and protect an ear from the bite of said teeth while enabling said teeth to hold said ear muffs in place.

2. The ear warmer of claim 1 and a flexible member joining the two leaves and fitting over the top of the ear of the wearer.

3. The ear warmer of claim 2 wherein said flexible member is a rubber band.

4. The ear warmer of claim 1 wherein each of said leaves has upstanding members thereon which interleave with upstanding members on the other leaf, and a hinge pin running through said upstanding members.

5. The ear warmer of claim 4 and a spring mounted on said hinge pin for urging said leaves to a closed position.

6. The ear warmer of claim 1 wherein said bonnet is a soft and flexible member having a central opening surrounded by an elastic band, said band stretching and enabling said opening to slip over an individually associated one of said leaves, each of said leaves having upstanding members thereon which interleave with upstanding members on the other of said leaves, a hinge pin running through said upstanding members, and a spring mounted on said hinge pin for urging said leaves to a closed position.

* * * * *